United States Patent [19]

Miller

[11] Patent Number: 5,280,243
[45] Date of Patent: Jan. 18, 1994

[54] SYSTEM FOR LOGGING A WELL DURING THE DRILLING THEREOF

[75] Inventor: Melvin Miller, Wynnewood, Pa.

[73] Assignee: Numar Corporation, Malvern, Pa.

[21] Appl. No.: 48,551

[22] Filed: Apr. 16, 1993

Related U.S. Application Data

[63] Continuation of Ser. No. 622,460, Dec. 5, 1990, abandoned.

[51] Int. Cl.$^5$ ............................................. G01R 33/20
[52] U.S. Cl. .................................. 324/303; 324/300; 73/151
[58] Field of Search ............... 324/300, 303, 318, 322; 73/152, 151

[56] References Cited

U.S. PATENT DOCUMENTS

| | | | |
|---|---|---|---|
| 3,083,335 | 3/1963 | Schuster | 324/0.5 |
| 3,205,477 | 9/1965 | Kalbfell | 73/152 |
| 3,258,681 | 6/1966 | Brown et al. | 324/0.5 |
| 3,360,716 | 12/1967 | Bloom et al. | 324/303 |
| 3,395,337 | 8/1968 | Varian | 324/303 |
| 3,402,344 | 9/1968 | Brown et al. | 324/303 |
| 3,483,465 | 12/1969 | Baker, Jr. | 324/0.5 |
| 3,597,681 | 8/1971 | Huckabay et al. | 324/0.5 |
| 3,617,867 | 11/1971 | Herzog | 324/303 |
| 3,667,035 | 5/1972 | Slichter | 324/303 |
| 4,350,955 | 9/1982 | Jackson et al. | 324/303 |
| 4,528,508 | 7/1985 | Vail, III | 324/303 |
| 4,560,663 | 12/1985 | Nicksic et al. | 436/25 |
| 4,629,986 | 12/1986 | Clow et al. | 324/303 |
| 4,710,713 | 12/1987 | Strikman | 324/303 |
| 4,714,881 | 12/1987 | Givens | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,785,245 | 11/1988 | Lew et al. | 324/307 |
| 4,825,163 | 4/1989 | Yabusaki et al. | 324/318 |
| 4,829,252 | 5/1989 | Kaufman | 324/309 |
| 4,875,013 | 10/1989 | Murakami et al. | 324/318 |
| 4,933,638 | 6/1990 | Kenyon et al. | 324/303 |
| 5,023,551 | 6/1991 | Kleinberg et al. | 324/303 |

FOREIGN PATENT DOCUMENTS

| | | | |
|---|---|---|---|
| 0295134 | 12/1988 | European Pat. Off. | G01V 3/32 |
| 1158959 | 5/1985 | U.S.S.R. | 324/303 |

OTHER PUBLICATIONS

Miller, M., et al.; "Spin Echo Magnetic Resonance Logging: Porosity and Free Fluid Index Determination", SPE20561.

Timur, A.; "Pulsed Nuclear Magnetic Resonance Studies of Porosity, Movable Fluid, and Permeability of Sandstones", SPE-AIME, Jun.; 1969, Journal of Petroleum Engineers.

Herrick, R., et al.; "An Improved Nuclear Magnetism Logging System and its Application To Formation Evaluation", SPE8361.

Jackson, J., et al.; "Remote (Inside-Out) NMR III. Detection of Nuclear Magnetic Resonance in a Remotely Produced Region of Homogeneous Magnetic Field", Academic Press, May, 1980.

*Primary Examiner*—Michael J. Tokar
*Assistant Examiner*—Raymond Y. Mah
*Attorney, Agent, or Firm*—Pennie & Edmonds

[57] ABSTRACT

Nuclear magnetic resonance well logging apparatus and a method of use for geophysical examination of a bore hole as the bore hole is drilled. The apparatus is connected to the drill bit to follow it through the bore hole as the bore hole is formed. The apparatus comprises a resilient, tubular, permanent magnet for generating a static magnetic field in the region of a portion of the bore hole adjacent the apparatus, which region includes materials sought to be analyzed, an antenna mounted on the magnet and connected to associated circuitry for exciting nuclei of the materials sought to be analyzed in the region, and a receiver connected to the antenna for receiving nuclear magnetic resonance signals from the excited nuclei and for providing an output signal indicative of properties of the materials sought to be analyzed.

53 Claims, 4 Drawing Sheets

SYSTEM FOR LOGGING A WELL DURING THE DRILLING THEREOF

This is a continuation of application Ser. No. 07/622,460, filed Dec. 5, 1990, now abandoned.

BACKGROUND OF THE INVENTION

This invention relates generally to well logging utilizing nuclear magnetic resonance, and more particularly to apparatus and methods for utilizing nuclear magnetic resonance to log a well as it is drilled.

The derivation of information relating to petroleum or other organic fuel deposits at an underground geological location is the subject of various technological approaches. For example, one common prior art technique to derive such information is known as nuclear magnetic resonance (NMR) logging. Basically, the NMR logging technique entails introducing a nuclear magnetic resonance logging apparatus or probe into a well or bore hole which has been drilled by conventional drilling equipment. The probe serves to excite the nuclei of materials in the surrounding geological structure so that various parameters, e.g., spin density, $T_1$ and $T_2$ relaxation, et., of the surrounding geological formation can be measured. From that data valuable information regarding the makeup of the structure, e.g., the amount of extractable oil, can be determined.

Examples of prior art NMR logging apparatus and methods are described in the following U.S. Pat. Nos. 3,508,438 (Alger et al), 3,617,867 (Herzog), 3,667,035 (Slichter), 4,350,955 (Jackson), 4,467,642 (Givens), 4,528,508 (Vail, III), 4,560,663 (Nicksic et al), 4,629,986 (Clow et al), 4,710,713 (Taicher et al), 4,713,881 (Givens), 4,717,878 (Taicher et al), and 4,933,638 (Kenyon et al).

While the apparatus and techniques disclosed above appear generally suitable for their intended purposes, they nevertheless suffer from one significant drawback. That drawback is that such prior art systems are not designed (and are generally unsuitable) for effecting the logging of the bore hole as it is drilled. Instead they are designed such that the bore hole is drilled first, the downhole drilling apparatus is then removed, and then the logging apparatus or probe is introduced into the bore hole and their measurements then are made therewith.

A much more desirable technology would permit the logging of the desired rock parameters during the actual drilling process. The measuring of such parameters of the geological structure adjacent the bore hole as the bore hole is drilled is sometimes referred to in the art as 37 measuring while drilling" (or its acronym "MWD") or "logging while drilling" (or its acronym "LWD"). Such procedure has been accomplished heretofore utilizing non-NMR based apparatus. For example, Teleco Oil Field Services, Inc., of 105 Pondview Drive, Meriden Conn. 06450, offers for sale a tool under the name "RGD (resistivity-gamma-directional) MWD tool". That device is described by Teleco as a multi-sensor tool which transmits real-time measurements to surface equipment for detection, decoding, displaying and archiving. The RGD tool consists of three downhole sensors installed in a forty-foot drill collar. The formation resistivity sensor and the gamma ray sensor are both located in a subassembly below the directional sensor and transmitter, and are placed as close as possible to the drill bit. The integrated assembly offers two options, namely, downhole data recording, or transmission of the MWD data uphole in the form of coded pressure pulses in the drilling mud. Data from the downhole tool and surface information (such as depth, rate-of-penetration, hookload and rpm) is then recorded by a range of cabin and non-cabin based surface data acquisition systems. Such surface systems present data on real-time logs and archive the data on either tape, floppy disk or both.

The major components of the downhole RGD tool include a transmitter which produces positive mud pulses in the drilling mud in response to digitally coded signals from the sensor. A mud circulation driven turbine provides power for the downhole assembly. The turbines are configured to manage flow ranges from 250 GPM to 1,100 GPM. A resistivity sensor is provided which is a sixteen-inch spacing short-normal resistivity sensor located in a subassembly below the transmitter and directional sensor. The natural gamma ray sensor Teleco provides is located midway between the resistivity electrodes so that both formation evaluation sensors simultaneously obtain their information at the same depth, thus eliminating the need to memorize either measurement. A tool orientation system is also provided which is comprised of a digital sensor system which measures tool orientation information (e.g., azimuth, and inclination).

Such downhole assemblies (DHA's) are configured inside a drill collar. MWD collars allow the drilling mud to flow around the various sensors. Most sensors are located in the wall of the drill collar adjacent the outer surface and often need electrical isolation from the collar.

While the foregoing tools may offer the advantage over wireline logging technology by enabling logging to be accomplished while drilling, such tools nevertheless suffer from certain natural limitations. Such limitations result primarily because they attempt to replicate the wireline logging tools which operate in a much more gentle environment than do MWD tools. The MWD/LWD tools require more complex, robust technology and thus they tend to be more expensive. To do an adequate petrophysical evaluation, a minimum of three types of measurements or logs are required, i.e., neutron, deep resistivity, and density. Moreover, such systems may not be sufficient to predict the amount of petroleum present because they lack certain key information, and thus are unable to predict the productivity qualities of the rocks.

NMR logging apparatus and techniques address those limitations by providing direct measurements of this key information. When synergized with the resistivity, gamma and directional MWD tools, a full petrophysical evaluation is possible. The value of this NMR apparatus is clearly demonstrated by comparing it to the wireline technology's ability to provide information on the pore structure and the fluids present. This is possible because of the NMR's ability to assess the rock's porosity system independent of the rock formation type. However, as mentioned earlier, prior art NMR logging systems have not permitted adoption of their measuring system to MWD/LWD technology.

OBJECTS OF THE INVENTION

It is a general object of this invention to provide an apparatus and a method of use for logging wells using nuclear magnetic resonance which overcomes the disadvantages of the prior art.

It is a further object of this invention to provide an apparatus and a method for drilling a well and at the same time logging the well using nuclear magnetic resonance.

It is a further object of this invention to provide an apparatus which is simple in construction yet effective for drilling a well at the same time that the well is logged using nuclear magnetic resonance.

It is yet a further object of this invention to provide nuclear magnetic resonance apparatus for logging a well which is rugged in construction and arranged to be connected to a drilling assembly so that logging can be performed at the same time that a well is being drilled thereby.

SUMMARY OF THE INVENTION

These and other objects of this invention are achieved by providing well logging apparatus and a method of use for effecting the geophysical examination of a bore hole as the bore hole is drilled.

The apparatus comprises logging means coupled to means for drilling the bore hole so that the logging means follows the drilling means through the bore hole. The logging means comprises first means, e.g., a flexible tubular permanent magnet, for generating a static magnetic field in the region of a portion of the bore hole adjacent the logging means, which region includes materials sought to be analyzed, second means, e.g., an antenna and associated components, for exciting nuclei of the materials sought to be analyzed in the region, and third means, e.g., the antenna and other associated components, for receiving nuclear magnetic resonance signals from the excited nuclei and for providing an output signal indicative of properties of the materials sought to be analyzed.

In accordance with one preferred aspect of this invention the apparatus is mounted closely adjacent the drill bit for rotational and longitudinal movement with the drill bit as it forms the bore hole. The apparatus can be operated at that time to generate the output signal indicative of properties of the materials sought to be analyzed in the region adjacent the apparatus.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
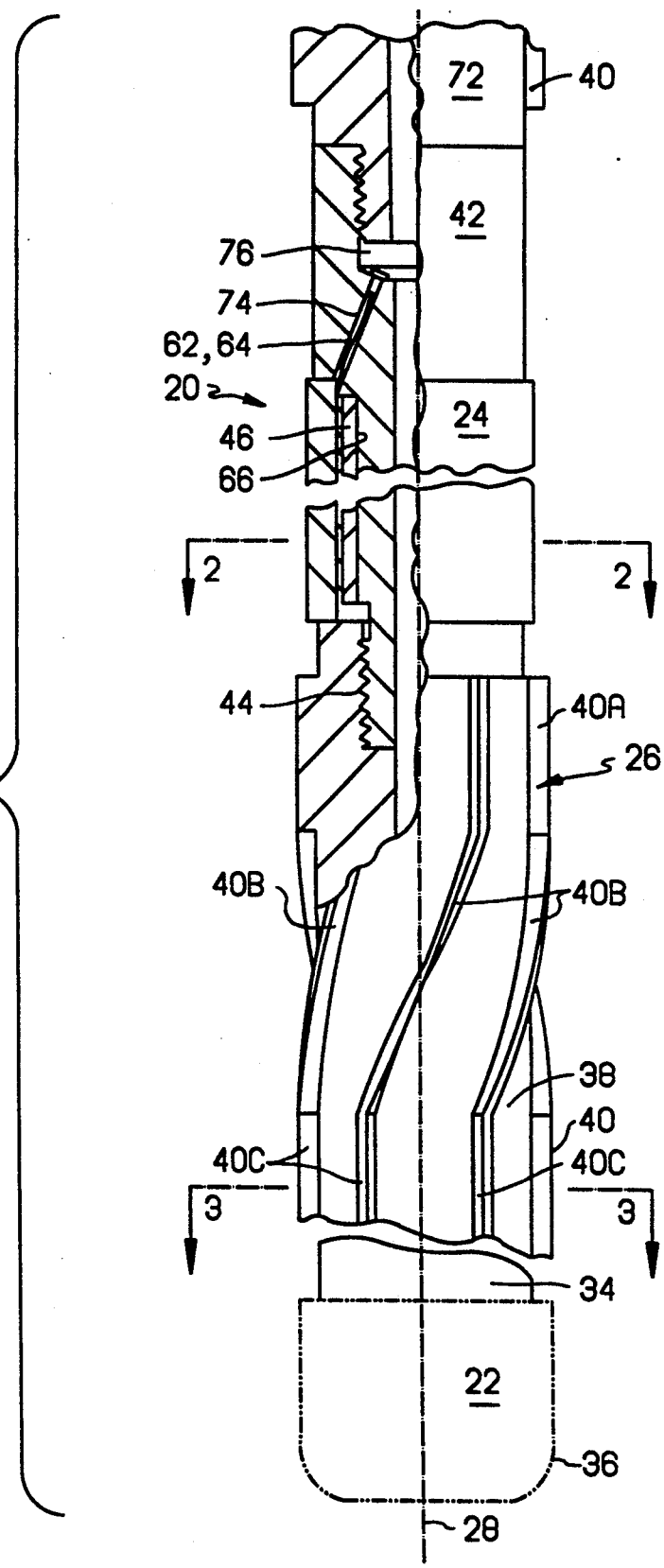
FIG. 1 is a side elevational view, partially in section, of the lower end of nuclear magnetic resonance apparatus for logging while drilling,, which is constructed in accordance with the subject invention.
Figure 2:
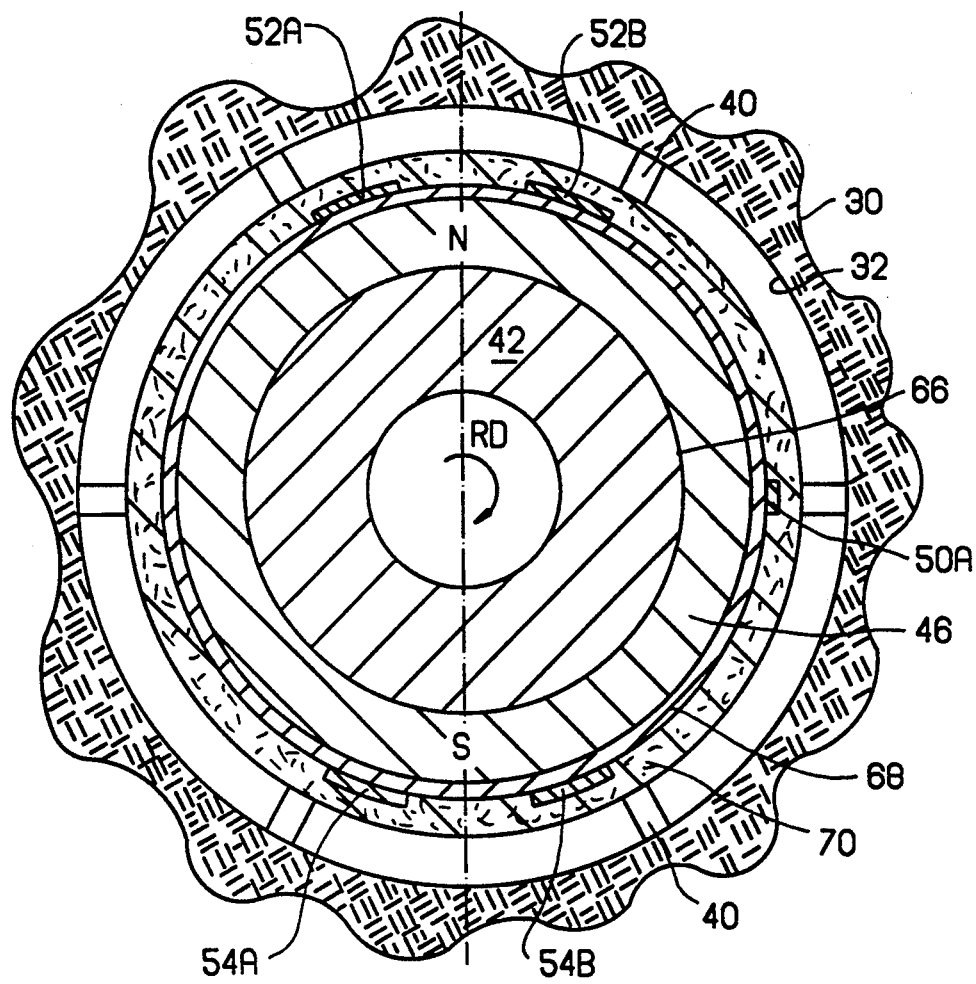
FIG. 2 is an enlarged sectional view taken along line 2—2 of FIG. 1.
Figure 3:
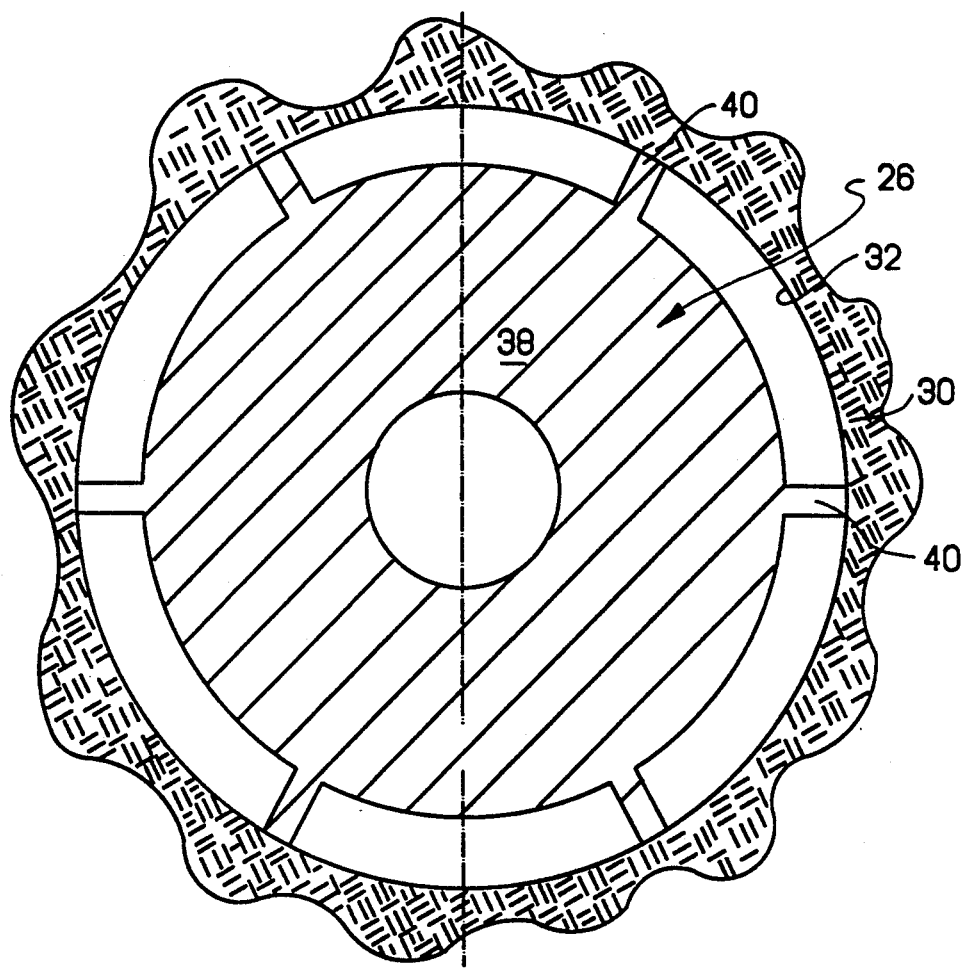
FIG. 3 is an enlarged sectional view taken along line 3—3 of FIG. 1.

Referring now to various figures of the drawing wherein like reference numerals refer to like parts there is shown at 20 in FIG. 1 apparatus for drilling a well while at the same time effecting the logging of the surrounding ground structure using nuclear resonance measuring techniques. The system 20 basically comprises drilling means 22, NMR logging means 24, and position stabilization means 26, all in an integrated package or assembly arranged to create a well or bore hole under power by a conventional drilling apparatus (not shown). Thus, the apparatus 20 is arranged to be rotated about its longitudinal axis 28 under power from the drilling apparatus to cause the drilling means 22 to bore into the ground 30 (FIGS. 2 and 3) at the situs of the geological structure (materials) sought to be analyzed to form the bore hole 32 (FIGS. 2 and 3).

The details of the NMR logging means 24 will be described later. Suffice it for now to state that such means includes a "probe" section made up of an assembly of a permanent magnet and an antenna (both to be described later) and a "control" section made up of associated electronic/electrical components. The probe section is constructed to produce a gradient static magnetic field in the radial direction, i.e., outward from the central longitudinal axis 28 of the apparatus. Moreover, that field has a static field direction substantially perpendicular to the longitudinal axis 28 and with a generally uniform amplitude along the azimuth with respect to that axis. The field is produced in the ground structure 30 which is adjacent the bore hole 32. The antenna of the probe serves to produce a radio frequency magnetic field in the ground structure adjacent the bore hole to excite nuclei of the material(s) sought to be analyzed. The direction of the radio frequency magnetic field is substantially perpendicular to both the longitudinal axis of the apparatus and to the static field direction. The antenna is coupled to the electronic/electrical components of the NMR logging means 24 to receive nuclear magnetic resonance signals from the material(s) to be analyzed, whereupon the electronic/electrical components provide output signals indicative of the properties of those materials.

As will be appreciated by those skilled in the art from the description of probe portion of the NMR logging means 24 to follow, the fields produced by such means are like those disclosed in the aforementioned U.S. Pat. No. 4,710,713 (which patent is assigned to the same assignee as this invention and whose disclosure is incorporated by reference herein). By so doing the apparatus 20 is able to examine the nature of material(s) in the geological formation in the vicinity of the bore hole in a region of generally cylindrical configuration extending about the bore hole. This volume is referred to hereinafter as the "sensitive volume." In the preferred embodiment of the invention described herein the creation of a bore hole of 10 inches (25.4 cm) diameter produces a sensitive volume of circular cylindrical configuration extending from 12 inches (30.5 cm) to 20 inches (50.8 cm) from the central longitudinal axis of the apparatus 20 and the bore hole.

Before discussing the details of the structure and operation of the system 20 it should be noted that in order to make magnetic resonance measurements of fluids, e.g., oil, in rock formations adjacent the bore hole while the apparatus 20 is being used three basic conditions must be satisfied. The first condition is that the static and alternating (rf) magnetic fields produced by the apparatus must remain orthogonal to each other while rotation of the apparatus 20 is accomplished. Thus, as will be seen hereinafter the external static and alternating fields produced by the NMR logging means 24 is symmetrical about the longitudinal axis of the apparatus. The second condition for effective operation is that the rotation of the drill portion 22 must be well below the Larmor frequency. As will be described in detail later, the Larmor frequency is in the range of 1 MHz while the tool rotation is less than ten Hz. Lastly, since drill collars are all made of electrically conductive steel to provide proper strength, and since it is well known that electro-magnetic waves have a difficulty penetrating electro-conductors, with the steel even affecting the electro-magnetic propagation when they are in close proximity, the probe portion of the NMR logging means 24 includes an RF antenna which is disposed on a non-conductive magnetic sleeve outside of a steel collar forming the probe.

Turning now to FIG. 1 it can be seen that the apparatus 20 is in the form of a steel casing made up of a plurality of longitudinally disposed sections forming and/or housing the drilling means 22, the NMR logging means 24, and the stabilizing means 26. In particular, the free end section of the system 20 is in the form of a tubular, steel, collar section 34 on which a drill bit 36 is mounted. The drill bit 36 and its supporting collar 34 form the heretofore identified drilling means 22. The drill bit 36 may be any type of conventional drill bit used for drilling oil well holes.

The drill bit collar 34 is mounted on the far (distal) end of a collar section 38. The section 38 is also a tubular member, preferably formed of steel, whose outer periphery is circular. A plurality of fins 40 project radially outward from the outer surface of the section 38. Each fin is an elongated member having a longitudinally extending end portion 40A, an angularly extending intermediate portion 40B, and a second, longitudinally extending end portion 40C. Thus, the end portions 40A and 40C of each fin are offset circumferentially from each other by the angularly extending intermediate portion. This fin arrangement forms the heretofore identified stabilization means and in so doing facilitates the stabilization of the spin of the apparatus 20 during the drilling/logging. Moreover, as shown clearly in FIG. 3 the fins are arranged so that their top surface engages the inner wall of the bore hole, thereby keeping the apparatus 20 centered in the bore hole as drilling and logging are accomplished.

The stabilizing collar section 38 is releasably secured to another collar section 42 via a threaded connector 44. The collar section 42 forms the heretofore identified probe portion of the NMR logging means 24 and hence includes the magnet and antenna assembly mentioned earlier. That assembly basically comprises a magnet 46 and a pair of antennae 48 and 50. As can be seen section 42 is a tubular member, preferably formed of stainless steel, having an externally threaded end 44 which extends into a correspondingly internally threaded throat at the proximal end of the stabilizing section 38.

The magnet 46 will be described later, suffice it for now to state that it comprises a tubular member which serves to create the static magnetic field in the sensitive volume. The antennae 48 and 50 are each mounted on the tubular magnet 46, in a manner also to be described later.

The antenna 48 serves as the means for creating the rf field in the sensitive volume in order to excite the nuclei of the material(s) sought to be analyzed therein. In addition, the antenna 48 serves as the means for receiving the NMR-signals produced by the excited nuclei. The antenna 50 serves as a calibration antenna, i.e., it and associate electronic means (not shown) effect the measurement of the electrical loading of the environment in order to calibrate the system 20.

Figure 4:
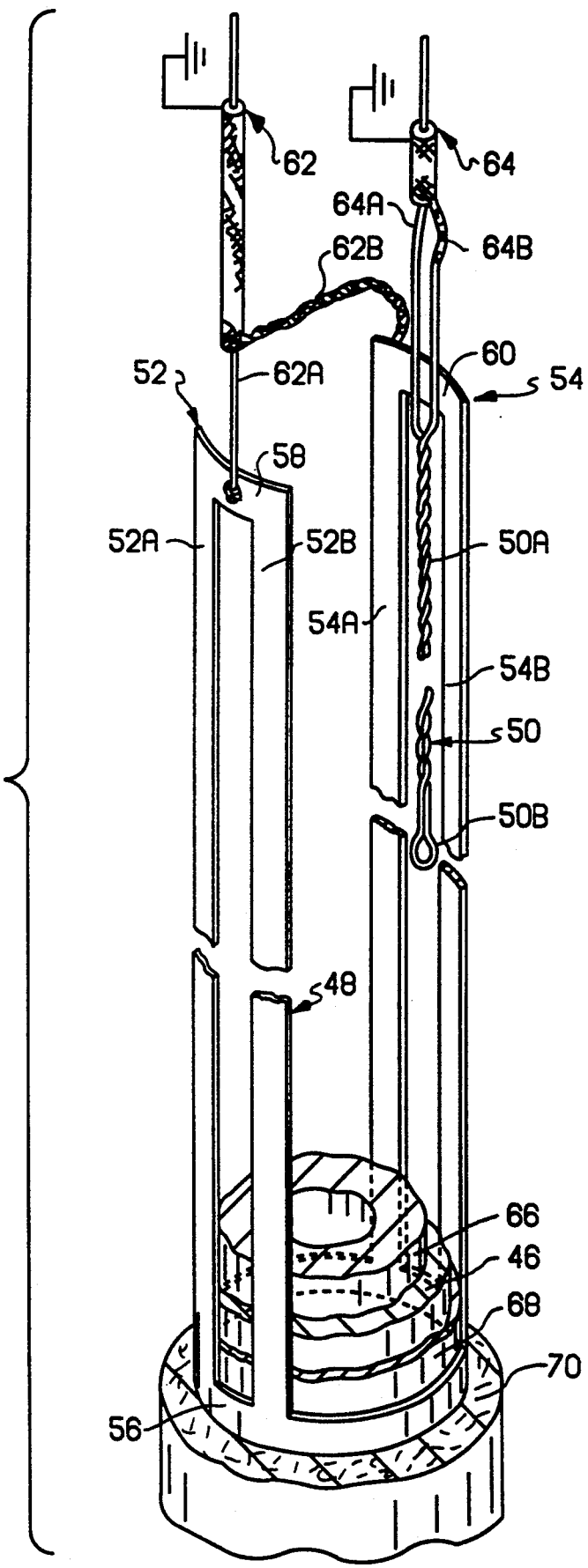
FIG. 4 is an enlarged isometric view partially in section of a portion of the apparatus shown in FIG. 1.

The details of the construction and arrangement of the antenna 48 will best be understood by reference to FIGS. 1, 3, and 4. Thus, as can be seen therein the antenna 48 comprises two pairs of parallely connected conductor pairs 52 and 54. The two pairs 52 and 54 are connected in series with each other to form a series/parallel antenna 48. The series/parallel antenna 48 is connected to associated electronic/electrical components of the system, e.g., a rf transmitter/receiver (not shown). Those components are preferably located within another collar section of the apparatus 20 (to be described later).

As can be seen clearly in FIG. 4 the conductor pair 52 is made up of two longitudinally extending electrical conductors 52A and 52B. These conductors are electrically connected at one end to a ring conductor 56. In a similar manner the conductor pair 54 is made up of two longitudinally extending electrical conductors 54A and 54B which are also electrically connected together at one end to the ring conductor 56. The other end of the conductors 52A and 52B are electrically connected to each other by a bridging conductor 58. In a similar manner the other end of the conductors 54A and 54B are electrically connected to each other by a bridging conductor 60. The bridging conductor 58 is in turn electrically connected to the central conductor 62A of a coaxial cable 62, while the bridging conductor 60 is electrically connected to the braided wire conductor 62B of that cable.

The two conductor pairs 52 and 54 of the antenna 48 are mounted on the magnet 46 of the collar section 42 at diametrically opposed positions with respect to each other (see FIGS. 2 and 4). In particular conductor pair 52 is disposed longitudinally along the north pole N of the magnet 46, while conductor pair 54 is located along the south pole S. In accordance with a preferred embodiment of this invention each of the conductors 52A and 52B is in the form of a thin strip whose width constitutes approximately 16 degrees of the circular periphery of the magnet 46 upon which the antenna is mounted. Moreover the distance separating the conductors 52A and 52B from each other is approximately 20 degrees. The conductors 54A and 54B are similarly constructed and oriented with respect to each other.

With the conductors 52A and 52B and the conductors 54A and 54B constructed as just described, the amplitude of the rf field produced by antenna 48 approximates a cosine distribution with regard to the rotation direction angle (the direction of that angle is indicated by the arrow designated as "RD" in FIG. 2). This serves to cancel certain higher order non-uniformities and results in maximizing the uniform magnetic field distribution in the sensitive volume.

As mentioned above the antenna is connected to the transmitter/receiver. In particular the conductor 62A is connected to the positive potential output/input terminal (designated by the "+" in FIG. 4) of the rf transmitter/receiver, while the conductor 62B is connected to ground. The transmitter/receiver may be of any suitable construction for producing the desired electrical signals to excite the nuclei of the material(s) in the sensitive volume and for providing electrical output signals representative of the NMR signals produced by the excited nuclei.

The calibration antenna 50 is a small antenna which basically comprises a twisted pair of thin electrical conductors 50A terminating at a looped end 50B. One of the conductors 50A is electrically connected to the central conductor 64A of another coaxial cable 64, while the other of the conductors 50A is electrically connected to the braided wire conductor 64B of that cable. The cable 64 is connected to suitable calibration circuitry (not shown) located within the collar section (to be described later) in which the other electronic/electrical components making up the system 20 are located. Thus, the braided conductor 64B of the cable is connected to ground and the conductor 64A is connected to a positive potential terminal (designated by the "+" in FIG. 4) of the calibration circuitry.

As best seen in FIG. 4 the magnet 46 basically comprises a thin walled cylindrical tube or sleeve which is formed of a non-conductive, permanent magnetic ferrite material, e.g., a combination of ferrite, barium, and strontium. Preferably the magnet has a uniform magnetization axis which is perpendicular to the longitudinal axis 28 of the apparatus 20. The magnet 46 is disposed in a longitudinally extending annular recess 66 extending about the collar section 42.

Inasmuch as the apparatus 20 is arranged to be rotated about its longitudinal axis to effect logging while drilling, the magnet 46 will be subjected to shock and vibration. Accordingly, it is preferred that the magnet 46 be somewhat flexible to absorb such shock and vibration. As an alternative the magnet may be composed of ceramic pieces or tiles which are held within or mounted on a tough, shock absorbing matrix material.

The outer surface of the magnet 46 is covered with a thin coating 68 formed of an electrically insulative material, e.g., fiberglass, Teflon, etc., having a thickness of approximately 100 mils. The antennae 48 and 50 are mounted on the coated outer surface 68 of the magnet and are electrically insulated therefrom by the coating 68. Each antenna extends longitudinally along the outer surface of the magnet, with the antenna 48 extending for substantially the entire length of the magnet and the antenna 50 extending for only a portion of the length of the magnet between the conductors 54A and 54B. In order to protect the magnet 46 and the antennae 48 and 50 mounted thereon, an electrically insulative, e.g., fiberglass, sleeve 70 is disposed about the magnet/antennae combination.

In accordance with a preferred embodiment of this invention the magnet 46 is approximately 183 cm long, the antenna 48 is approximately 137 cm long, and the antenna 50 is approximately 76 cm long. Moreover, the outside diameter of the annular recess 66 is approximately 12 cm. The outside diameter of the coated magnet is approximately 16 cm. The outside diameter of the sleeve 70 is approximately 18 cm.

The electronic/electrical components which make up the system 20, e.g., the transmitter/receiver, controller, etc., are located within a "control" collar section 72. The control section 72 is a hollow member, formed of steel, and preferably includes a chamber (not shown) in which the system's electronic/electrical components are mounted. That chamber is resistant to high pressures frequently encountered in drilling operations, thereby protecting the somewhat fragile electronic/electrical components from such pressures.

The cables 62 and 64 extend from the antennae 48 and 50, respectively, through an angularly extending bore 74 in the collar section 42. This bore communicates with an annular space 76 at the interface of the sections 42 and 72, with the antenna leads (i.e. the cables 62 and 64) extending through the bore 74, the annular space 76, and into the interior of the section 72 for connection to the electronics therein.

Like section 42, the section 72 includes plural stabilizing fins 40 mounted on its outer periphery to expedite the stabilization of the apparatus' spin centered within the bore hole.

Without further elaboration the foregoing will so fully illustrate my invention that others may, by applying current or future knowledge, adopt the same for use under various conditions of service.

What I claim is:

1. Well logging apparatus for geophysical examination of a bore hole having a longitudinal axis, said apparatus comprising logging means having a longitudinal axis substantially aligned with the longitudinal axis of the bore hole and drilling means having a drill bit mounted on a drill collar extending through the bore hole, said logging means coupled to said drilling means so that said logging means follows said drilling means through said bore hole as said drilling means forms said bore hole, said logging means comprising:
    (a) first means for generating a static magnetic field in the region of a portion of the bore hole adjacent the logging means, which region includes materials sought to be analyzed;
    (b) second means for generating a radio frequency magnetic field substantially symmetric about the longitudinal axis of the logging means for exciting nuclei of the materials sought to be analyzed in said region, said second means being located outside said drill collar; and
    (c) third means for receiving nuclear magnetic resonance signals from the excited nuclei and for providing and output signal indicative of properties of the materials sought to be analyzed.

2. The apparatus of claim 1 wherein said drilling means rotates to form said bore hole and said logging means is coupled to said drilling means to rotate therewith.

3. The apparatus of claim 1 wherein said drilling means comprises a drill bit mounted on a drill collar, said first means comprising a tubular member disposed about a portion of said drill collar remote from said drill bit, said tubular member comprising at least one permanent magnet.

4. The apparatus of claim 3 wherein said tubular member includes resilient portions.

5. The apparatus of claim 2 wherein said drilling means comprises a drill bit mounted on a drill collar, said first means comprising tubular magnet means disposed about a portion of said drill collar closely adjacent said drill bit, said magnet means comprising at least one permanent magnet.

6. The apparatus of claim 5 wherein said magnet means includes resilient portions.

7. The apparatus of claim 2 wherein said first means generates a gradient static magnetic field in said region, and wherein said second means generates a radio frequency magnetic field in said region to excite said nuclei therein, said fields being orthogonal to each other.

8. The apparatus of claim 7 wherein said logging means comprises antenna means mounted on said first means, said antenna means forming a portion of said second and said third means.

9. The apparatus of claim 7 wherein said drilling means comprises a drill bit mounted on a drill collar, said first means comprising tubular magnet means disposed about a portion of said drill collar closely adjacent said drill bit, said tubular magnet means comprising at least one permanent magnet.

10. The apparatus of claim 9 wherein said magnet means is resilient.

11. The apparatus of claim 9 wherein said logging means comprises antenna means mounted on said magnet means, said antenna means forming a portion of said second and said third means.

12. The apparatus of claim 10 wherein said logging means comprises antenna means mounted on said magnet means, said antenna means forming a portion of said second and said third means.

13. The apparatus of claim wherein said antenna means is electrically isolated from said magnet means.

14. The apparatus of claim 12 wherein said antenna means is electrically isolated from said magnet means.

15. The apparatus of claim 13 wherein said magnet means is an elongated member having a longitudinal central axis and wherein said antenna means comprises at least one elongated member extending along said magnet means parallel to said axis.

16. The apparatus of claim 13 wherein said magnet means is an elongated member having a longitudinal central axis and wherein said antenna means comprises at least one elongated member extending along said magnet means parallel to said axis.

17. The apparatus of claim 14 wherein said magnet means is an elongated member having a longitudinal central axis and wherein said antenna means comprises at least one elongated member extending along said magnet means parallel to said axis.

18. The apparatus of claim 5 wherein said drill collar is a cylindrical member having a central longitudinal axis and including a longitudinally extending annular recess in which said magnet means is located.

19. The apparatus of claim 18 wherein said logging means comprises antenna means mounted on said magnet means, said antenna means forming a portion of said second and said third means.

20. The apparatus of claim 19 wherein said antenna means is electrically isolated from said magnet means.

21. The apparatus of claim 19 wherein said magnet means is an elongated member having a longitudinal central axis and a cylindrical outer surface extending around said axis, and wherein said antenna means comprises at least one elongated member extending along the outer surface of said magnet means parallel to said axis.

22. The apparatus of claim 20 wherein said magnet means is an elongated member having a longitudinal central axis and a cylindrical outer surface extending around said axis, and wherein said antenna means comprises at least one elongated member extending along the outside surface of said magnet means parallel to said axis.

23. The apparatus of claim 21 additionally comprising an electrically insulative and non-magnetic sleeve disposed about said magnet means and said antenna means.

24. The apparatus of claim 23 wherein said sleeve is formed of fiberglass.

25. The apparatus of claim 23 additionally comprising a layer of an electrically insulative and non-magnetic material between said magnet means and said antenna means.

26. The apparatus of claim 24 additionally comprising a layer of an electrically insulative and non-magnetic material between said magnet means and said antenna means.

27. The apparatus of claim 22 additionally comprising an electrically insulative and non-magnetic sleeve disposed about said magnet means and said antenna means.

28. The apparatus of claim 27 wherein said sleeve is formed of fiberglass.

29. The apparatus of claim 27 additionally comprising a layer of an electrically insulative and non-magnetic material between said magnet means and said antenna means.

30. The apparatus of claim 28 additionally comprising a layer of an electrically insulative and non-magnetic material between said magnet means and said antenna means.

31. The apparatus of claim 8 wherein said antenna means produces a good approximation of a pulse dipole field.

32. The apparatus of claim 8 wherein said antenna means comprises two pairs of elongated conductors disposed immediately adjacent said first means.

33. The apparatus of claim 32 wherein said first means comprises an elongated tubular permanent magnet having a longitudinal central axis and wherein said pairs of elongated conductors extend along said permanent magnet parallel to said central axis.

34. The apparatus of claim 33 wherein each of said conductors is of a relatively narrow width defined by an arc of a first predetermined polar angle measured with respect to said axis, and wherein the distance between the centers of the arcs of each pair of conductors is a second predetermined polar angle measured with respect to said axis.

35. The apparatus of claim 34 wherein said first predetermined polar angle is approximately fifteen degrees.

36. The apparatus of claim 35 wherein said second polar angle is approximately twenty degrees.

37. The apparatus of claim 35 wherein said second polar angle is approximately twenty degrees.

38. The apparatus of claim 32 wherein said pairs of electrical conductors are connected in series with each other, and wherein said conductors of each pair are connected in parallel with each other.

39. The apparatus of claim 38 wherein said first means comprises an elongated tubular permanent magnet having a longitudinal central axis and wherein said pairs of elongated conductors extend along said permanent magnet parallel to said central axis.

40. The apparatus of claim 39 wherein each of said conductors is of a relatively narrow width defined by an arc of a first predetermined polar angle measured with respect to said axis, and wherein the distance between the centers of the arcs of each pair of conductors is a second predetermined polar angle measured with respect to said axis.

41. The apparatus of claim 40 wherein said first predetermined polar angle is approximately fifteen degrees.

42. The apparatus of claim 40 wherein said second polar angle is approximately twenty degrees.

43. The apparatus of claim 41 wherein said second polar angle is approximately twenty degrees.

44. The apparatus of claim 5 wherein said tubular magnet includes a longitudinal central axis, and wherein said antenna means comprises two pairs of elongated conductors extending along said tubular magnet parallel to said axis.

45. The apparatus of claim 44 wherein said pairs of electrical conductors are connected in series with each other, and wherein said conductors of each pair are connected in parallel with each other.

46. The apparatus of claim 45 wherein each of said conductors is of a relatively narrow width defined by an arc of a first predetermined polar angle measured with respect to said axis, and wherein the distance between the centers of the arcs of each pair of conductors is a second predetermined polar angle measured with respect to said axis.

47. The apparatus of claim 46 wherein said first predetermined polar angle is approximately fifteen degrees.

48. The apparatus of claim 46 wherein said second polar angle is approximately twenty degrees.

49. The apparatus of claim 47 wherein said second polar angle is approximately twenty degrees.

50. A method of using nuclear magnetic resonance logging apparatus for effecting the geophysical examination of a bore hole having a longitudinal axis, said logging apparatus having a longitudinal axis substantially aligned with the longitudinal axis of the bore hole and a means for generating a radio frequency magnetic field, said method comprising:
(a) coupling said logging apparatus to a drilling apparatus having a drill bit mounted on a drill collar extending through the bore hole such that said means for generating the radio frequency magnetic field is located outside said drill collar for rotational and longitudinal movement therewith,
(b) forming a bore hole by rotating said drill bit, and
(c) operating said logging apparatus to:
(1) generate a static magnetic field in the region of a portion of the bore hole adjacent said logging apparatus, which region includes materials sought to be analyzed,
(2) generate a radio frequency magnetic field substantially symmetric about the longitudinal axis of the logging apparatus to excite nuclei of the materials sought to be analyzed in said region, and
(3) receive nuclear magnetic resonance signals from the excited nuclei for providing an output signal indicative of properties of the material sought to be analyzed.

51. The method of claim 50 wherein the examination of said bore hole is accomplished as it is drilled by said drill bit.

52. The method of claim 50 wherein said static magnetic field is a gradient field.

53. The method of claim 51 wherein the examination of said bore hole is accomplished as it is drilled by said drill bit.

* * * * *